(12) United States Patent
Kandt

(10) Patent No.: US 7,173,161 B1
(45) Date of Patent: Feb. 6, 2007

(54) BANDAGE FOR RELIEF OF THE MUSCULATURE IN MUSCLE FIBRE TEARS

(75) Inventor: Olaf Kandt, Herzogenrath (DE)

(73) Assignee: Beiersdorf AG, Hamburg (DE)

( * ) Notice: Subject to any disclaimer, the term of this patent is extended or adjusted under 35 U.S.C. 154(b) by 1219 days.

(21) Appl. No.: 09/688,658

(22) Filed: Oct. 16, 2000

(30) Foreign Application Priority Data

Oct. 20, 1999 (DE) .......................... 199 50 509

(51) Int. Cl.
*A61F 13/00* (2006.01)

(52) U.S. Cl. ................ 602/41; 602/5; 602/61; 602/62

(58) Field of Classification Search .......... 602/1, 602/5, 61, 62, 75–77; 604/289
See application file for complete search history.

(56) References Cited

U.S. PATENT DOCUMENTS

| 3,888,244 | A |   | 6/1975  | Lebold ............. 128/77 |
| 3,926,186 | A |   | 12/1975 | Nirschl ............ 128/165 |
| 5,472,413 | A |   | 12/1995 | Detty ............... 602/26 |
| 5,512,039 | A | * | 4/1996  | White ............... 602/26 |
| 5,843,025 | A | * | 12/1998 | Shaari .............. 602/53 |
| 5,968,002 | A | * | 10/1999 | Morrisseau ......... 602/62 |
| 6,248,932 | B1 | * | 6/2001 | Himmelsbach ...... 602/41 |

FOREIGN PATENT DOCUMENTS

| CH | 672 061  | 10/1989 |
| DE | 37 10 115 | 9/1988 |
| DE | 196 46 740 | 5/1998 |
| EP | 0 842 648 A1 | 5/1998 |

OTHER PUBLICATIONS

English–language counterpart to EP 0 842 648 A1 (Specification—U.S. Ser. No. 08/966,217, filed Nov. 7, 1997).
English–language counterpart to DE 196 46 740 (Specification—U.S. Ser. No. 08/966,127, filed Nov. 7, 1997.
English–language abstract of DE 37 10 115, dated Sep. 22, 1988.
English–language abstract of CH 672 061, dated Oct. 31, 1989.

* cited by examiner

*Primary Examiner*—Nicholas D. Lucchesi
*Assistant Examiner*—Lalita M. Hamilton
(74) *Attorney, Agent, or Firm*—Norris McLaughlin & Marcus

(57) ABSTRACT

Bandage 100 for relief of the musculature, comprising an essentially rectangular central portion 1 on whose transverse edges 11, 12 a total of four tensioning straps 21, 22, 23, 24 are secured, the central portion 1 being smoothed on opposite the injured site in the muscle tissue of the limb, the two proximal tensioning straps 21, 22 being guided in a diagonal movement in the distal direction and the two distal tensioning straps 23, 24 being guided in a diagonal movement in the proximal direction in such a way that the two proximal tensioning straps 21, 22 cross each other proximally of the injured site, the two distal tensioning straps 23, 24 cross each other distally of the injured site, and in each case one proximal tensioner 21, 22 and one distal tensioner 23, 24 cross each other laterally of the injured site, so that the injured site is left free, with the ends 31, 32, 33, 34 of the tensioning straps 21, 22, 23, 24 being secured on the bandage 100.

8 Claims, 6 Drawing Sheets

BANDAGE FOR RELIEF OF THE MUSCULATURE IN MUSCLE FIBRE TEARS

The invention relates to a bandage for relief of the musculature in muscle fibre tears, particularly in the limbs of the human body.

When the muscle apparatus of the human body is exposed to stresses, especially in sports activities, pulled muscles, muscle strains, muscle fibre tears and muscle bundle tears commonly occur. These indications in some cases involve considerable pain, especially muscle fibre tears arising upon acute or chronic overstraining of a muscle. In addition to the pains already mentioned, such as pain on movement, pain on tensing, pain caused by pressure, and pain on extension, the symptoms also include haematoma.

In popular sports and in competitive sports, as well as in everyday life, there are only a few injuries which occur as frequently as muscle fibre tears and distorsion trauma or ligament tears of the upper leg.

Therapeutically, muscle fibre tears are treated by, among other things, immobilizing the muscle for 24 to 48 hours, cold applications to the injured area, and elevation of the affected limb. Compression dressings are also used. Ointment dressings and Unna's paste dressings are also known, and also the use of physical therapy which generally includes stimulation or targeted treatment of destroyed physiological functions by physical natural means, for example water, heat and cold, light, air, statically/mechanically (massage), with dynamic forces, mineral springs or electricity.

The design of the compression dressing to be applied is adapted to the injured part of the body, be it the thigh or lower leg, the upper arm or forearm.

Compression dressings are normally applied which are formed using non-adhesive and self-adhesive dressings. The non-adhesive dressings are wrapped in circles round the limb concerned, leaving the site of the injury free. Securing is carried out using circular straps of the adhesive material which cross each other in the manner of ears of corn, these straps being arranged distally and proximally of the injured site in order to obtain relief of the damaged musculature, while the actual injury site remains free at all times. This site can be treated with ointments to assist its recovery, the ointment being able to be applied without changing the whole dressing. After the dressing has been applied, however, this free site should likewise be closed in order to rule out the formation of a fenestration oedema.

The functional dressing technique described, also called taping, is a treatment method for prevention and therapy of injuries, diseases and lesions of the locomotor apparatus. The aim of taping is to purposefully simulate the capsular ligament structures and in so doing to achieve selective support and stabilizing.

The actual tape dressing is applied in strips made of preferably non-elastic self-adhesive tapes, so-called tensioners, or in conjunction with self-adhesive tapes with short-stretch elasticity. It protects, supports and relieves vulnerable, damaged or impaired parts of a functional unit. It permits selective loading within the pain-free range of movement, but prevents extreme or painful movements.

However, the application of such dressings requires expert skill and experience and for this reason cannot generally be done by lay persons with no taping experience.

This also applies to the known dressings for treating muscle fibre tears or pulled muscles. The lay person is not readily able to apply the dressing, described in detail, without medical or expert assistance.

Ortheses represent a further means of treatment, although, from a purely medical point of view, the orthesis is a form of treatment which, for these indications, normally represents a subsidiary treatment.

Depending on their design and on the indication for which they are intended, orthopaedic bandages exert a fixing, guiding, bracing and/or supporting action on the limbs of the human body. These medical bandages must have a three-dimensional shape to correspond to the anatomical circumstances in order to be able to act externally on the human body with a form fit and a force fit.

The object of the invention is to develop a bandage which can be successfully used for pulled muscles, muscle strains, muscle fibre tears and muscle bundle tears, without exhibiting the abovementioned shortcomings. In particular, the bandage should be able to be applied without problem, afford a high degree of wearing comfort and be simple to readjust, if this proves necessary. In addition, the bandage should be able to relieve the injured site.

This object is achieved by means of a bandage as specified in the main claim. The dependent claims relate to advantageous developments of the bandage.

Accordingly, the invention relates to a bandage for relief of the musculature, comprising an essentially rectangular central portion on whose transverse edges a total of four tensioning straps are secured preferably in the corner areas. The central portion is smoothed on opposite the injured site in the muscle tissue of the limb. The two proximal tensioning straps are guided in a diagonal movement in the distal direction and the two distal tensioning straps are guided in a diagonal movement in the proximal direction in such a way that the two proximal tensioning straps cross each other proximally of the injured site, the two distal tensioning straps cross each other distally of the injured site, and in each case one proximal tensioner and one distal tensioner cross each other laterally of the injured site, so that the injured site is left free, with the ends of the tensioning straps being secured on the bandage.

In this way, an open portion is obtained over the injured site, so that the straps can exert their action directly on the skin, in order thereby to achieve effective relief of the injured site.

The central portion of the bandage should be made of a firm but stretchable material, preferably a longitudinally elastic woven or knitted fabric which, if appropriate, can also have a slight transverse elasticity, in particular based on cotton. The longitudinal elasticity preferably corresponds to that of so-called short-stretch bandages, i.e. bandages with an extensibility of approximately 60% to 90%.

In an advantageous embodiment of the bandage, in each case a proximal tensioning strap and a distal tensioning strap come together laterally of the injured site to form a single strap, so that two Y-shaped tensioning straps are obtained.

For this purpose, the straps have velcro fastener tapes, preferably at their ends, and are cured on themselves by means of fastener eyelets.

By means of this Y-shaped strap, the bandage can be applied with the desired pressure and the complete musculature thus relieved in just two manoeuvres.

In the V area, the strap advantageously consists of a soft, thin and short-stretch elastic material such as a woven or knitted fabric. In some cases, elastic or plastic parts can also advantageously act on user comfort in the longitudinal or transverse direction. Moreover, nonwovens or foams or paper can also be used if these have sufficient strength. Non-elastic materials are preferably used for the ends of the straps.

The material can advantageously consist of cotton and can have a maximum tensile force of not less than 50 N/cm and a maximum tensile force extension of less than 20%.

The straps should only be arranged in semicircles around the lower leg in order to exclude congestion.

In order to exert a high tensile force, fastener eyelets can be arranged on the central portion, the straps being guided through these eyelets and then secured on themselves. The fastener eyelets allow the straps not to be applied in circles, which considerably reduces the risk of congestion.

For the thigh variant of the bandage according to the invention, it is possible to dispense with the fastener eyelets, because straps with wide velcro ends are advantageous here.

The bandage can be secured especially well on the limb concerned if a velcro fastener tape is arranged at the proximal end of the central portion and a velcro fastener tape is arranged at the distal end of the central portion. Slippage is thereby ruled out. The fastener tapes should preferably enclose no more than ¾ of the limb in order to avoid congestion.

Particularly in the case where the bandage lies across the tibia, a vertically extending, soft portion is fitted in the central portion in order to avoid pressure sores on the tibia.

To make supportive treatment measures easier and to prevent development of a fenestration oedema, it is possible, in a further advantageous embodiment of the bandage, to arrange a fastening flap on the central portion, which flap reversibly covers the injured site.

The fastening flap is preferably sewn onto the central portion, and in such a way that the tensioning straps or the Y-shaped tensioning strap can be guided through between central portion and fastening flap, so as not to impede the tightening of the bandage. For this purpose, it is simplest for the fastening flap to be sewn to the central portion only along the edge area.

It is thus possible to access this site at any time without having to remove the bandage. The formation of a fenestration oedema is reliably avoided. The fastening flap should preferably also be made of a material which is relatively strong and has a short stretching.

The fastening flap can be provided with a soft pad so that the injured site can be additionally compressed. The pad can at the same time serve as an ointment support. The pad is advantageously secured on the fastening flap by means of a velcro fastener so that it can be quickly and easily replaced. The pad can also be designed with a double wall or have a sewn-on pocket in order to be able to introduce cooling elements into the pad or into the pocket to ensure primary care. A suitable material for forming the pad is, for example, a textile-lined latex foam which is suitably flexible and can be adapted well to strongly contoured regions of the body. Such a latex foam can be obtained from the Beiersdorf company under the name "Leukotape Foam®".

Moreover, in a preferred variant, lateral stabilizers are arranged on the bandage, for example made up of thin rolls of plastic.

In summary, it can be stated that the bandage according to the invention can be used for pulled muscles, muscle strains, muscle fibre tears and muscle bundle tears excellently and without contraindication.

A further advantageous use of the bandage is in combination with an anti-embolism stocking, as is offered, for example, by the Beiersdorf company under the name "Comprinet® S" or "Comprinet®".

The principle of the bandage according to the invention is based on the mode of action of the tape dressing technique very successfully used for the stated indications.

By bringing the injured muscle fibres into apposition, pain relief is achieved in the injured area. The pain relief is not permanent, however, but occurs only when the injured muscle fibres are loaded upon contraction of the musculature.

Whenever the area of the injured muscle is loaded, the patient experiences relief at the injured site, i.e. a marked reduction in pain in the injured area, particularly when walking.

This in turn has the consequence that the patient or sportsperson, in everyday movements, for example when walking, running or driving a car etc., will be physiologically motivated by the pain reduction and will be able to recover normal use of his/her leg at an earlier stage.

The bandage according to the invention can be applied in only a few manoeuvres. In addition, because of the high degree of flexibility, a wide range of patients can be covered by only a small number of sizes.

A further advantage of the bandage, and one not expected by the skilled person, is that the bandage can be used in any desired way, for example turned through 180° or wrapped at any desired angle around the limb, without having to make alterations to the bandage.

Particularly advantageous embodiments of the bandage are explained in greater detail with reference to the figures described below, without thereby unnecessarily limiting the invention.

BRIEF DESCRIPTION OF THE DRAWINGS

In FIG. 1, the bandage 100 is shown in the simplest embodiment, with four tensioning straps 21, 22, 23, 24. The bandage 100 for relief of the musculature comprises an essentially rectangular central portion 1 on whose transverse edges 11, 12 a total of four tensioning straps 21, 22, 23, 24 are secured in the corner areas.

Figure 1:
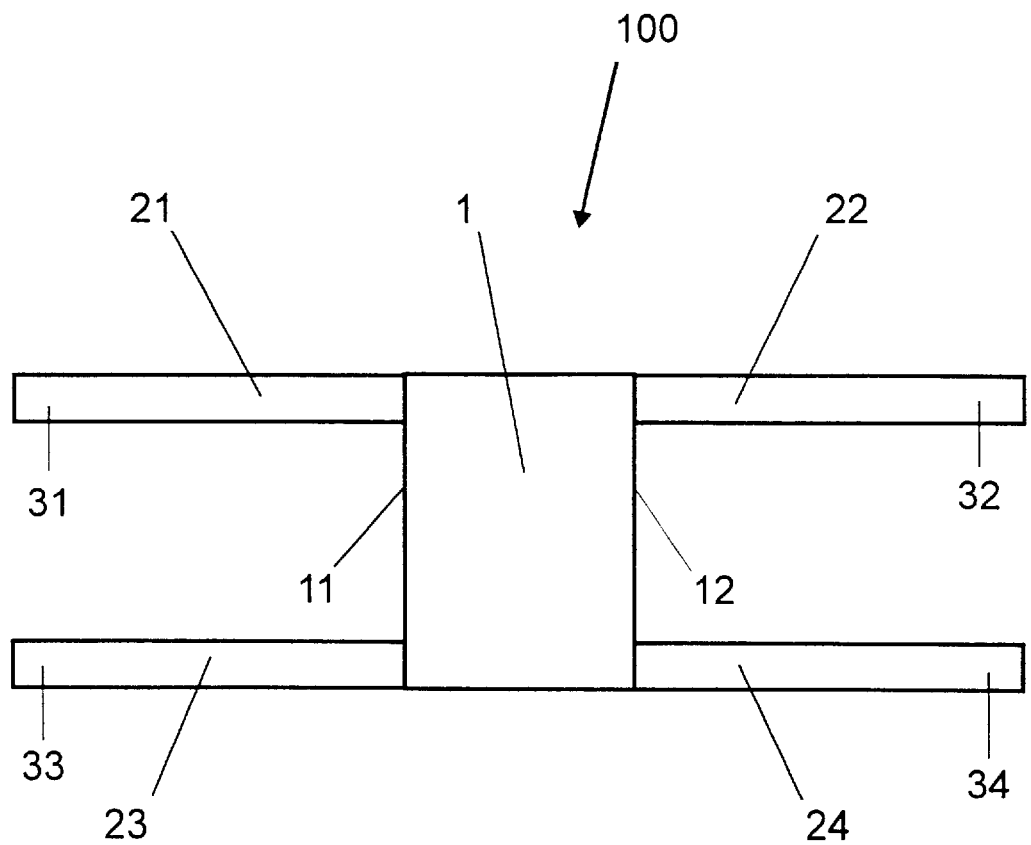
FIG. 1 shows the bandage in the simplest embodiment with four tensioning straps.

When applying the bandage to one of the arms or one of the legs, the central portion 1 is smoothed on opposite the injured site in the muscle tissue of the limb. The two proximal tensioning straps 21, 22 are guided in a diagonal movement in the distal direction and the two distal tensioning straps 23, 24 are guided in a diagonal movement in the proximal direction in such a way that the two proximal tensioning straps 21, 22 cross each other proximally of the injured site, the two distal tensioning straps 23, 24 cross each other distally of the injured site, and in each case one proximal tensioner 21, 22 and one distal tensioner 23, 24 cross each other laterally of the injured site, so that the injured site is left free. The ends 31, 32, 33, 34 of the tensioning straps 21, 22, 23, 24 are finally secured on the bandage 100. The ends 31, 32, 33, 34 are preferably provided with a velcro surface for this purpose.

Figure 2:
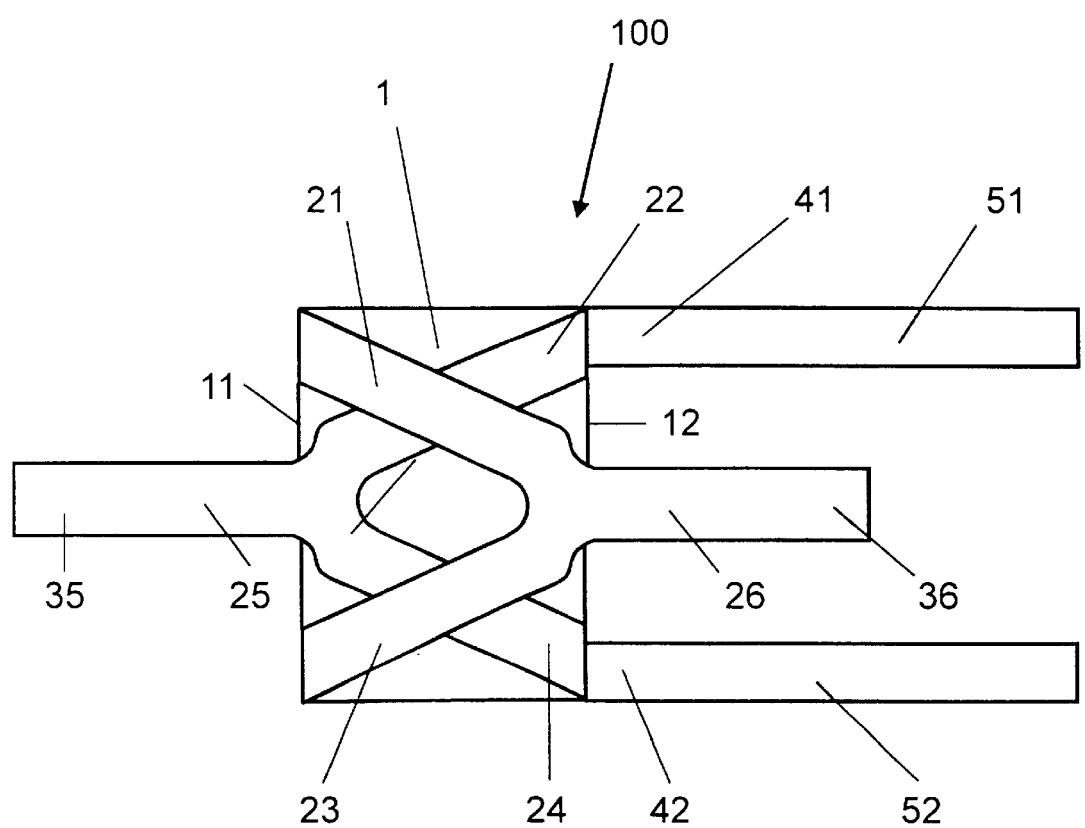
FIG. 2 shows the bandage in an advantageous embodiment with the Y-shaped tensioning straps.

FIG. 2 shows the bandage 100 in a first advantageous embodiment. On the essentially rectangular central portion 1, on whose transverse edges 11, 12 a total of four tensioning straps 21, 22, 23, 24 are once again secured, a velcro fastener tape 41 is additionally arranged at the proximal end of the central portion 1 and a velcro fastener tape 42 is arranged at the distal end of the central portion 1. The velcro fastener tapes 41, 42 have velcro surfaces 51, 52 approximately over their entire length in order to ensure a secure fit of the bandage on the limb.

In this particularly preferred variant of the bandage 100, in each case a proximal tensioning strap 21, 22 and a distal tensioning strap 23, 24 come together laterally of the injured site to form a single strap, so that two Y-shaped tensioning straps 25, 26 are obtained. The tensioning straps 25, 26 have velcro fastener tapes 35, 36 at their ends and are secured on themselves by means of fastener eyelets which are situated on the reverse of the central portion 1.

Figure 3:
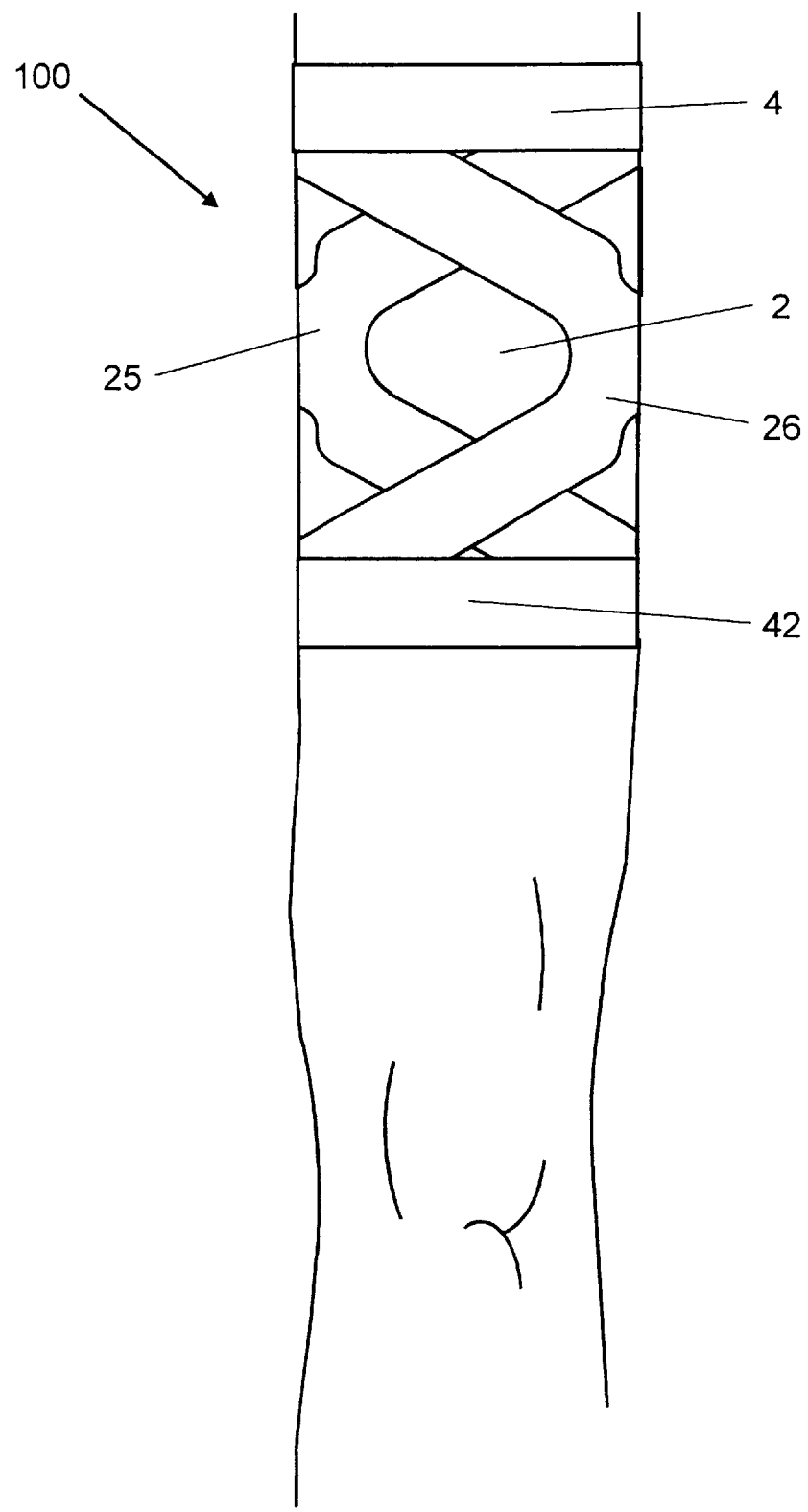
FIG. 3 shows the bandage in the advantageous embodiment with the y-shaped tensioning straps according to FIG. 2, applied to the right thigh of a patient, the injured site being located anteriorly in the muscle tissue of the thigh.

FIG. 3 shows the bandage 100 in the advantageous embodiment with the Y-shaped tensioning straps 25, 26 according to FIG. 2, the bandage 100 being applied to the right thigh of a patient. The injured site 2 (muscle fibre tear) is located anteriorly in the muscle tissue of the thigh.

By means of the tightened tensioning straps 25, 26, the injured muscle fibres are brought into apposition, so that pain relief in the injured area 2 is achieved. The pain relief is not permanent, however, but occurs only when the injured muscle fibres are loaded upon contraction of the musculature.

Enclosing the bandage 100 by means of the velcro fastener tapes 41, 42 secures the bandage 100 in its position.

Figure 4:
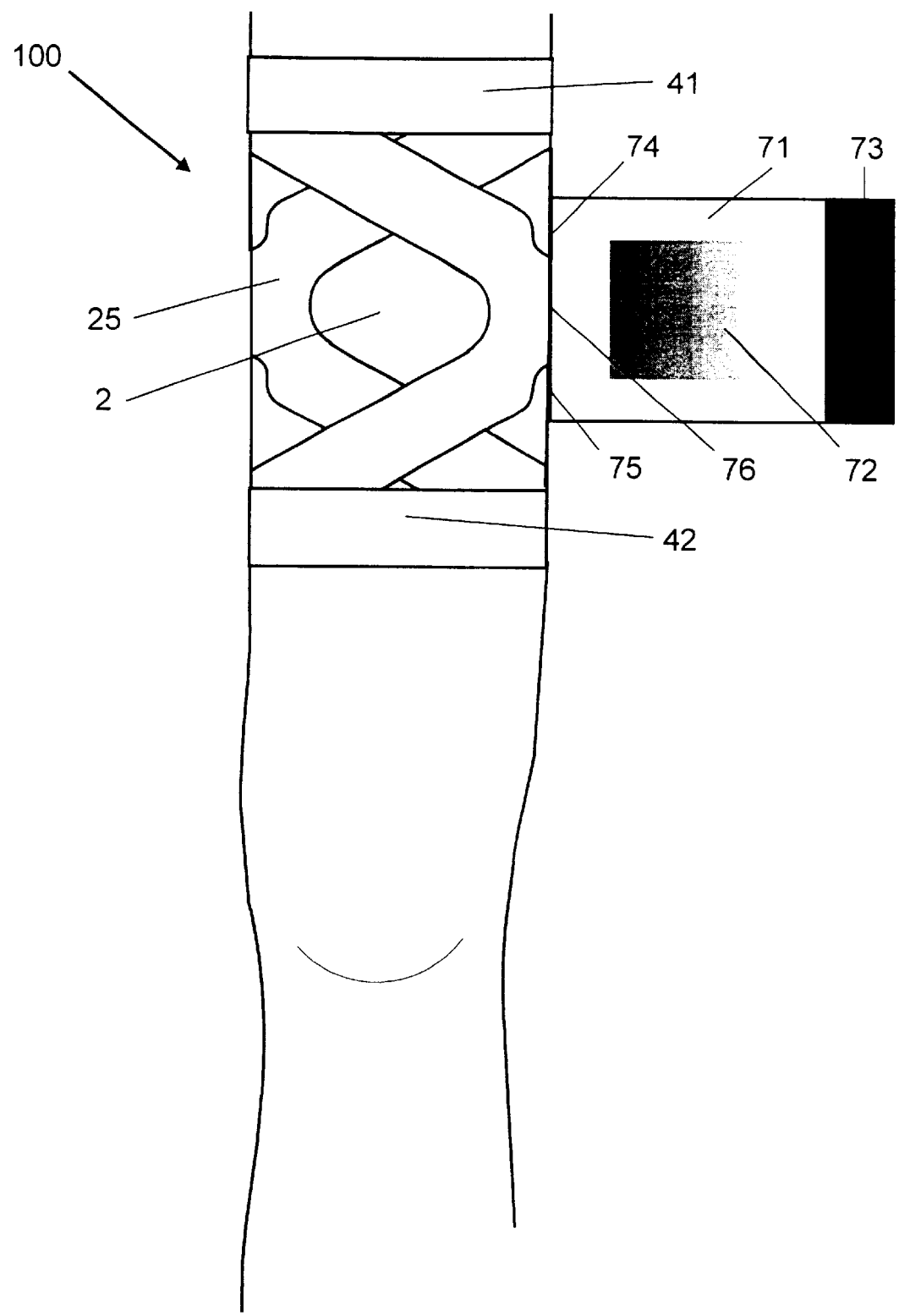
FIG. 4 shows the bandage in a further advantageous embodiment with the y-shaped tensioning straps according to FIG. 2, and with a fastening flap, applied to the right thigh of a patient, the injured site being located posteriorly in the muscle tissue of the thigh.

In FIG. 4, the bandage 100 is shown in a further advantageous embodiment with the Y-shaped tensioning straps 25, 26 according to FIG. 2 and with a fastening flap 71. The bandage 100 is applied to the right thigh of a patient, the injured site 2 being located posteriorly in the muscle tissue of the thigh. The fastening flap 71 is secured on the central portion 1, preferably sewn on as customary, and in such a way that the tensioning strap 26 can be guided between central portion 1 and fastening flap 71 so as not to impede the tightening of the tensioning strap 26. The seam with which the fastening flap 71 is secured on the central portion 1 is interrupted at the midpoint so that two partial seams 74 and 75 are obtained. The tensioning strap 26 is guided through the resulting gap 76, that is to say between central portion 1 and fastening flap 71.

A soft pad 72 is present on the fastening flap 71 in order to increase the compression on the injured site 2.

To close the fastening flap 71, a velcro surface 73 is further provided which can be secured on the bandage 100 after the fastening flap 71 has been folded round.

Figure 5:
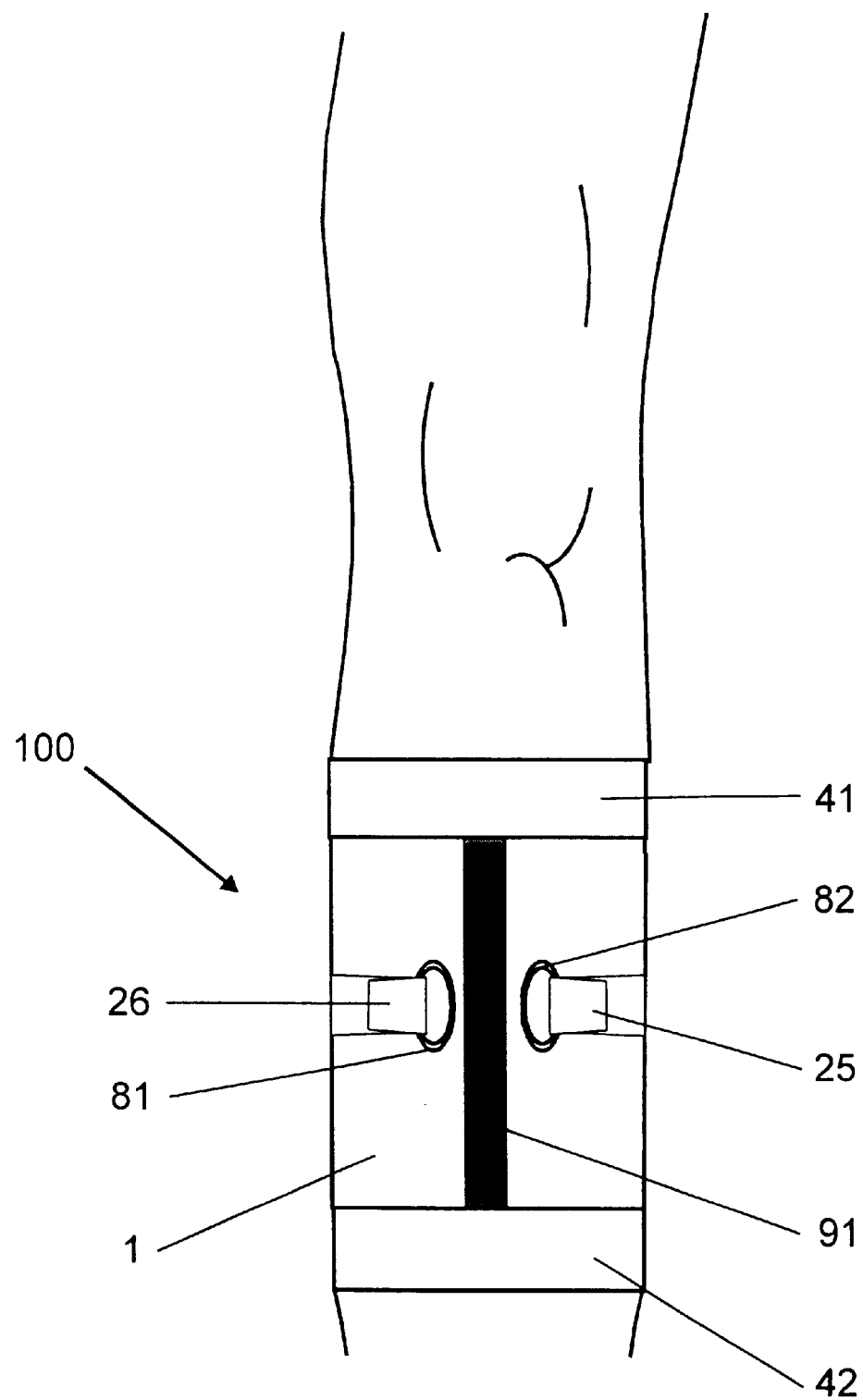
FIG. 5 shows the bandage in a further advantageous embodiment with the y-shaped tensioning straps which are closed by means of fastener eyelets, and with the soft portion fitted, applied to the right lower leg of a patient, the injured site being located posteriorly in the muscle tissue of the calf.

In FIG. 5, the bandage 100 is shown in a further advantageous embodiment, said bandage 100 having the Y-shaped tensioning straps 25, 26 which are closed by means of fastener eyelets 81, 82, and the soft portion 91 fitted in the central portion 1. The bandage 100 is applied to the right lower leg of a patient, the injured site being located posteriorly in the muscle tissue of the calf.

The fastener eyelets 81, 82 are secured on the outer side of the central portion 1, once again preferably sewn on. The tensioning straps 25, 26 are guided through the eyelets 81, 82, strongly tightened so that the necessary pressure builds up, and closed on themselves by means of the velcro ends 35, 36.

Since the bandage 100 lies over the tibia, the vertically extending, soft portion 91 is fitted in the central portion 1 in order to avoid pressure sores on the tibia.

Figure 6:
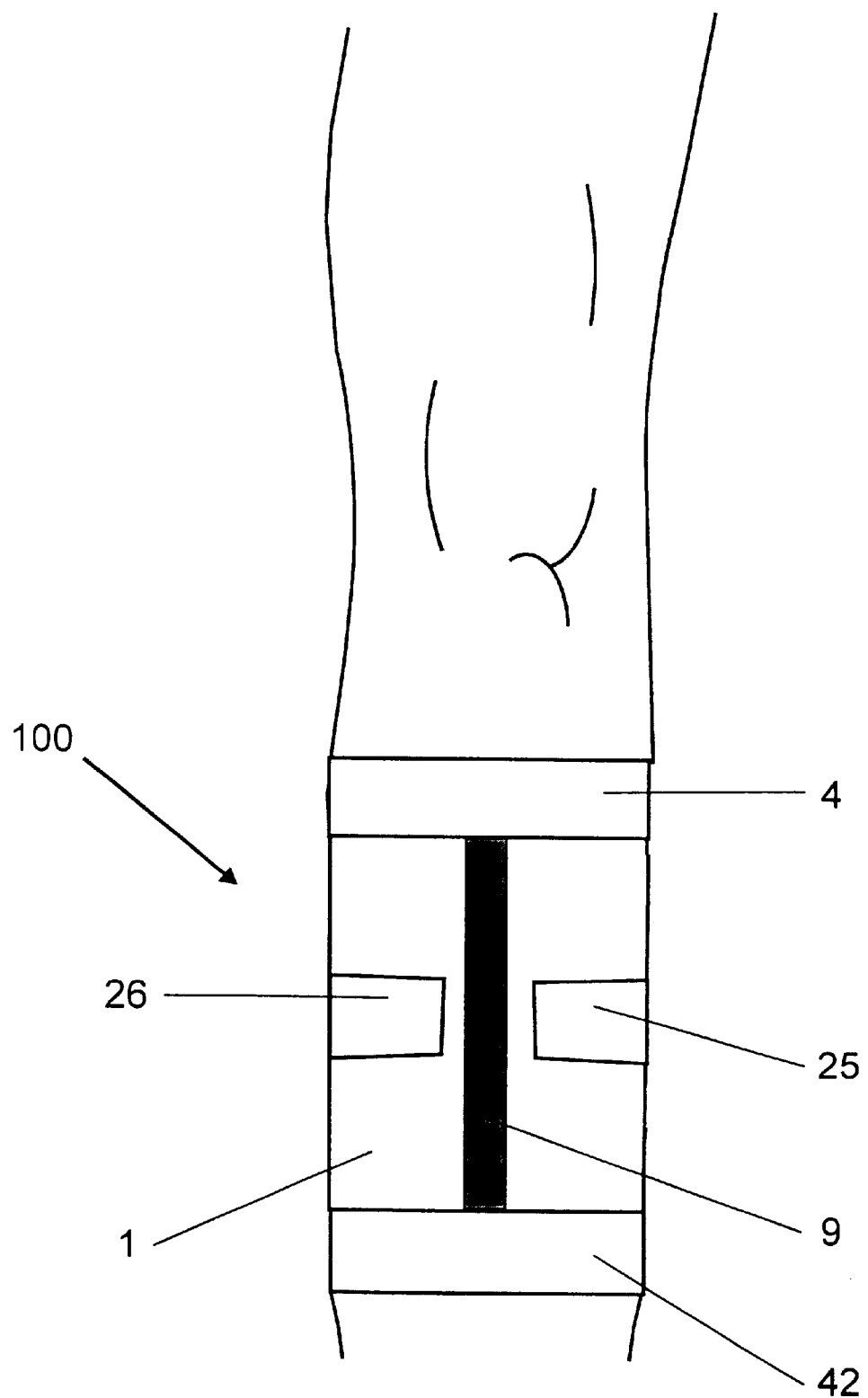
FIG. 6 shows the bandage in an advantageous embodiment, simplified compared to the bandage in FIG. 5, applied to the right lower leg of a patient, the injured site being located posteriorly in the muscle tissue of the calf.

Finally, FIG. 6 shows the bandage 100 in a further advantageous embodiment. The bandage 100 shown is simpler than the bandage 100 in FIG. 5, said bandage 100 once again being applied to the right lower leg of a patient, and the injured site being located posteriorly in the muscle tissue of the calf. This bandage 100 does not include the fastener eyelets. The pressure is built up by the tensioning straps 25, 26 being tightened. Particularly in the case of milder injuries to the muscle tissue, it is sufficient to fix the tensioning straps 25, 26 on themselves by means of velcro surfaces.

What is claimed is:

1. Bandage 100 for relief of the musculature, comprising an essentially rectangular central portion 1 on whose transverse edges 11, 12 a total of four tensioning straps 21, 22, 23, 24 are secured, wherein straps 21, 22 are proximal tensioning straps and straps 23, 24 are distal tensioning straps, the central portion 1 being smoothed on opposite the injured site in the muscle tissue of the limb, the two proximal tensioning straps 21, 22 being guided in a diagonal movement in the distal direction and the two distal tensioning straps 23, 24 being guided in a diagonal movement in the proximal direction in such a way that the two proximal tensioning straps 21, 22 cross each other proximally of the injured site, the two distal tensioning straps 23, 24 cross each other distally of the injured site, and in each case one proximal tensioner 21, 22 and one distal tensioner 23, 24 cross each other laterally of the injured site, so that the injured site is left free, with the ends 31, 32, 33, 34 of the tensioning straps 21, 22, 23, 24 being secured on the bandage 100 and wherein a proximal tensioning strap 21, 22 and a distal tensioning strap 23, 24 come together laterally of the injured site to form a single strap, so that two Y-shaped tensioning straps 25, 26 are obtained.

2. Bandage according to claim 1, wherein a vertically extending, soft portion 91 is fitted in the central portion 1.

3. Bandage according to claim 1, wherein a fastening flap 71 is arranged on the central portion 1 and reversibly covers the injured site.

4. Bandage according to claim 1, wherein lateral stabilizers are arranged on the bandage 100.

5. A method for relieving pain due to pulled muscles, muscle strains, muscle fibre tears or muscle bundle tears, which comprises applying a bandage according to claim 1 to the area affected by said pain.

6. The method of claim 5, wherein said bandage is applied in combination with an anti-embolism stocking.

7. Bandage according to claim 1 wherein the rectangular central portion 1 has a longitudinal elasticity of approximately 60%–90%.

8. Bandage according to claim 1 wherein the V-area of the Y-shaped tensioning straps have a maximum tensile force of 50 N/cm and a maximum tensile force of extension of less than 20%.

* * * * *